US010675336B2

(12) United States Patent
Kline

(10) Patent No.: US 10,675,336 B2
(45) Date of Patent: Jun. 9, 2020

(54) GLYCOSIDASE REGIMEN FOR THE TREATMENT OF CHRONIC VIRAL INFECTION

(71) Applicant: Ellis Kline, Pendleton, SC (US)

(72) Inventor: Ellis Kline, Pendleton, SC (US)

( * ) Notice: Subject to any disclaimer, the term of this patent is extended or adjusted under 35 U.S.C. 154(b) by 0 days.

(21) Appl. No.: 16/204,398

(22) Filed: Nov. 29, 2018

(65) Prior Publication Data

US 2019/0091305 A1   Mar. 28, 2019

Related U.S. Application Data

(63) Continuation of application No. 14/431,249, filed as application No. PCT/US2013/061966 on Sep. 26, 2013, now abandoned.

(60) Provisional application No. 61/707,252, filed on Sep. 28, 2012.

(51) Int. Cl.
*A61K 39/00* (2006.01)
*A61K 38/47* (2006.01)
*A61K 45/06* (2006.01)

(52) U.S. Cl.
CPC .............. *A61K 39/00* (2013.01); *A61K 38/47* (2013.01); *A61K 45/06* (2013.01); *C12Y 302/01018* (2013.01); *Y02A 50/411* (2018.01); *Y02A 50/415* (2018.01); *Y02A 50/463* (2018.01)

(58) Field of Classification Search
None
See application file for complete search history.

(56) References Cited

U.S. PATENT DOCUMENTS

| | | | |
|---|---|---|---|
| 5,326,749 A | 7/1994 | Yamamoto | |
| 5,558,863 A | 9/1996 | Kline et al. | |
| 5,736,133 A * | 4/1998 | Kline | A61K 38/47 424/94.61 |
| 6,977,169 B2 | 12/2005 | Kline | |
| 7,842,314 B2 | 11/2010 | Kline | |
| 7,892,752 B2 | 2/2011 | Dwek et al. | |
| 8,747,919 B2 * | 6/2014 | Uto | A61K 35/16 424/725 |
| 2001/0036455 A1 | 11/2001 | Kline | |
| 2002/0164321 A1 | 11/2002 | Gallina | |
| 2008/0181913 A1 | 7/2008 | Dwek et al. | |
| 2010/0147571 A1 | 9/2010 | Wong et al. | |
| 2011/0038856 A1 | 2/2011 | Drachman et al. | |

FOREIGN PATENT DOCUMENTS

| | | |
|---|---|---|
| CN | 1473847 A | 2/2004 |
| CN | 1473848 A | 2/2004 |
| CN | 101214252 B | 3/2011 |
| WO | 1992003164 A1 | 3/1992 |
| WO | 1992018158 A1 | 10/1992 |
| WO | 1998046262 A1 | 10/1998 |
| WO | 2004062565 A2 | 7/2004 |
| WO | 2013038997 A1 | 3/2013 |
| WO | WO 2013/038997 * | 3/2013 |
| WO | 2014113641 | 7/2014 |

OTHER PUBLICATIONS

Newstead et al., The Journal of Biological Chemistry, Apr. 4, 2008, 283(14):9080-9088. (Year: 2008).*
SIGMA Product Specification Sheet (no date provided).*
Bean, Clinical Microbiology Reviews, 1992, 5(2):146-182. (Year: 1992).*
Ruby et al., J. Exp. Med., Nov. 3, 1997, 186(9):1591-1596. (Year: 1997).*
Hu H., et al., "Infectivities of Human and Other Primate Lentiviruses are Activated by Desialylation of the Virion Surface," Journal of Virology, vol. 70, No. 11, Nov. 1996, pp. 7462-7470.
Montefiori, D.C., et al., "Complement-Mediated Binding of Naturally Glycosylated and Glycosylation-Modified Human Immunodeficiency Virus Type 1 to Human CR2 (CD21)," Journal of Virology, vol. 67, No. 5, May 1993, pp. 2699-2706.
Supplementary partial European Search Report, EP Application No. 13840384.5, dated Feb. 12, 2016, 7 pages.
Kalra et al., "Mucin Impedes Cytotoxic Effect of 5-FU Against Growth of Human Pancreatic Cancer Cells" Overcoming Cellular Barriers for Therapeutic Gain, British Journal of Cancer, Nature Publishing Group, GB, vol. 97, No. 7, 2007, pp. 910-918.
Supplementary partial European Search Report, EP Application No. 14740546.8, dated Sep. 7, 2016, 5 pages.
International Search Report, PCT/US13/61966, 4 pages, dated Feb. 4, 2014.
Miyagi, et al., "Sialidase Significance for Cancer Progression", Glycoconj J, 2012, pp. 1-11.
Liang, et al., "Monocyte Differentiation Up-Regulates the Expression of the Lysosomal Sialidase, Neu1, and Triggers Its Targeting to the Plasma Membrane via Major Histocompatibility Complex Class II-Positive Compartments", The Journal of Biological Chemistry, 2006, vol. 281, No. 37, pp. 27526-27538.
Amith et al., "Dependence of Pathogen Molecule-Induced Toll-like Receptor Activation and Cell Function on Neu1 Sialidase", Glycoconj J, 2009, pp. 1197-1212.
McCormack, et al., "Toll-like Receptors and NOD-like Receptors in Rheumatic Diseases", Arthritis Research & Therapy, 2009, vol. 11, No. 243, pp. 1-8.
Li et al., "The Sialidases of Clostridium Perfringens Type D Strain CN3718 Differ in Their Properties and Sensitivities to Inhibitors", Applied and Environmental Microbiology, vol. 80, No. 5, pp. 1701-1709, (2014).

(Continued)

*Primary Examiner* — Nicole Kinsey White
(74) *Attorney, Agent, or Firm* — Morgan, Lewis & Bockius LLP

(57) ABSTRACT

In various aspects, the invention relates to immune tolerant glycosidase therapy. The invention provides methods for treating or preventing infectious disease, including chronic viral infections, and highly contagious infectious agents that present an ongoing challenge for the immune system. The compositions and treatment regimens find use with other antiviral or antimicrobial therapies, as well as in conjunction with vaccination to boost effectiveness and/or extend the duration of protective effect. In certain embodiments, the regimen described herein reduces or eliminates the need for administration of other traditional antiviral or antimicrobial therapies. In various embodiments, the invention finds use in immunocompromised patients to boost immune function.

20 Claims, 3 Drawing Sheets

(56) References Cited

OTHER PUBLICATIONS

International Search Report, PCT/US14/11995, 4 pages, dated Apr. 4, 2014.
Alley et al., "Effectiveness of Neuraminidase in Experimental Immunotherapy of Two Murine Pulmonary Carcinomas;" Cancer Res. 37(1): 95-101, Jan. 1977.
Arcaro et al., ß-Galactosidase and α-Mannosidase Inhibit Formation of Multicellular Nodules in Breast Cancer Cell Cultures, AntiCancer Research 24: 139-144 (2004).
Varki, et al., "Multifarious roles of sialic acids in immunity," Ann. N.Y. Acad. Sci. 1253 (2012) 16-36.
Tringali et al., "Silencing of membrane-associated sialidase Neu3 diminishes apoptosis resistance and triggers megakaryocytic differentiation of chronic myeloid leukemic cells K562 through the increase of ganglioside GM3," Cell Death and Differentiation, (2009) 16, 164-174.
Pappu et al., "Alteration of Cell Surface Sialylation Regulates Antigen-Induced Naive CD8+ T Cell Responses," The Journal of Immunology, 2004, 173: 275-284.
Han, "Enhancement of Delayed Skin Hypersensitivity by Neuraminidase in Cancer Patients," Clin. exp. Immunol., (1974) 18, 95-100.
Chemaly et al., "Neuraminidase Inhibitors Improve Outcome of Patients with Leukemia and Influenza: An Observational Study," Clinical Infectious Diseases, 2007;44:964-7.
Chang et al., "Leukocyte inflammatory responses provoked by Pneumococcal Sialidase," mBio 3(1):e00220-11. doi:10.1128/mBio. 00220-11, pp. 1-10, Jan./Feb. 2012.
Cassidy et al., "The Sialic Acids: VI. Purification and Properties of Sialidase from Clostridium Perfringens," The Journal of Biological Chemistry, vol. 240, No. 9, pp. 3501-3506, Sep. 1965.
Homer et al., Production of Specific Glycosidase Activities by Streptococcus Intermedius Strain UNS35 Grown in the Presence of Mucin, J. Med. Microbiol., 1994, vol. 41, pp. 184-190.
Kim, et al., "Tumor necrosis factor blockade and the risk of viral infection," Nat Rev Rheumatol. Mar. 2010 ; 6(3):165-174.
Seyrantepe, et al., Regulation of Phagocytosis in Macrophages by Neuraminidase 1, The Journal of Biological Chemistry, 2010, vol. 285, No. 1, pp. 206-215.
Iwamori, et al., AArthrobacter ureafaciens sialidase isoenzymes, L, M1 and M2, cleave fucosyl GM1, Glycoconjugate Journal, Jan. 1997, vol. 14, Issue 1, pp. 67-73. Abstract Only.

* cited by examiner

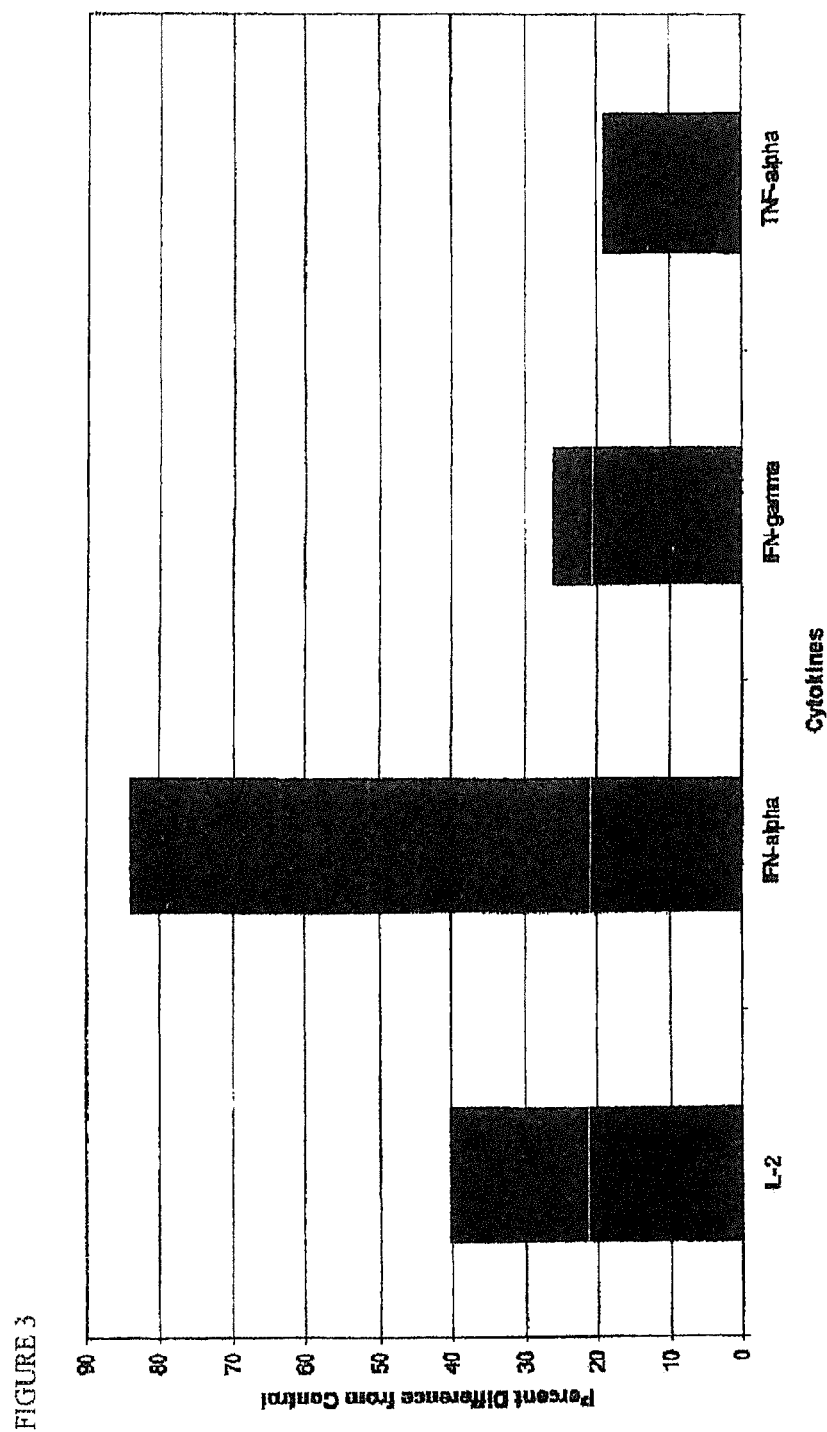

GLYCOSIDASE REGIMEN FOR THE TREATMENT OF CHRONIC VIRAL INFECTION

PRIORITY

This Application is a continuation of U.S. application Ser. No. 14/431,249, filed Mar. 25, 2015, which is a National Stage Entry of PCT/US2013/061966, filed Sep. 26, 2013, which claims priority to, and the benefit of, U.S. Provisional Application No. 61/707,252, which was filed Sep. 28, 2012, which is hereby incorporated by reference in its entirety.

FIELD OF THE INVENTION

The present invention relates to treatment and prevention of disease, and particularly the prevention, treatment and management of infectious disease, including chronic and non-chronic viral infections and other infectious disease with a glycosidase therapy.

BACKGROUND

Patients with chronic infections (such as chronic viral infections such as HIV, HSV, hepatitis virus, HPV, etc.) if effectively treated to reverse the disease trajectory or disease state, still require long-term disease management. However, continued administration of chemotherapeutic, monoclonal, or cytokine therapies can result in pathogen resistance, toxic effects for the patient including immune suppression, loss of effectiveness over time, and can be cost prohibitive for many patients. For example, antiretroviral (ARV) therapy, although successful in slowing the progression of AIDS, has transformed the disease into a chronic disease requiring long term treatment, and a basic acceptance of the very significant side effects and enormous cost of the drugs. Atun and Bateringaya. *Building a during response to HIV/AIDS: implications for health systems, J. Acquir Immune Defic. Syndr.* 57 Suppl. 2:S91-5 (2011). A more effective long term disease management of such infectious disease requires an active agent that maintains effectiveness over time, and which is substantially non-toxic or not immune suppressing for the patient, and ideally is coat effective.

In addition, treating or preventing certain infectious or epidemic illnesses, including Influenza, SARS, and the common cold, require long term boosts to the immune system to prevent infection, or prevent severe illness. This is especially true for the immune compromised, since available small molecule therapies can exacerbate the immune deficiency, and vaccines may be only marginally effective. Such a need is particularly high when vaccine is in short supply or unavailable.

There is a need for effective prevention, treatment and/or management of infectious disease, including management of chronic infections, and controlling highly contagious infectious diseases.

SUMMARY OF INVENTION

In various aspects, the invention provides compositions and methods for treating or preventing infectious disease, including chronic infections, and highly contagious infectious agents that present an ongoing challenge for the immune system or public health generally. The compositions and treatment regimens described herein may find use with other antiviral or antimicrobial therapies, as well as in conjunction with vaccination (e.g., non-adjuvant-containing vaccination) to boost vaccine effectiveness and/or extend the duration of protective effect. The treatment comprises in vivo administration of a glycosidase enzyme regimen (e.g., a regimen of one or more glycosidase enzymes) to the patient. In various embodiments, the glycosidase regimen is not targeted by the patient's immune system. In various embodiments, the glycosidase regimen provides one or more glycosidase enzymes active for removal of one or more terminal glycosyl groups on mammalian cells (e.g., immune cells), infected cells, or other glycosylated targets leading to immune activation. The glycosidase therapy elicits immune signaling cascades via its action on immune cells. Targeted terminal glycosyl groups may comprise, for example, sialosyl, beta-galactosyl, N-acetylgalactosamino, fucosyl, glucosyl, N-acetylglucosamino, and mannosyl residues, among others. Thus, the glycosidase regimen can include, in various embodiments, one or more of neuraminidase, galactosidase, N-acetylgalactosidase, fucosidase, glucosidase, N-acetylglucosaminidase, and mannosidase, among others. Without wishing to be bound by theory, the regimen increases immune signaling by removing effective amounts of glycosyl structures (e.g., sialic acid) from the surface of immune cells, infected cells, and/or other glycosylated targets. In this manner, the glycosidase regimen orchestrates or programs an effective immune response, allowing antigenic targeting of infected cells as well as eliciting proper levels of cytokine/chemokine cascades for therapy. In these or other embodiments, the glycosidase enzymes include at least one enzyme specific for a prominent terminal glycosyl residue (e.g., neuraminidase and/or galactosidase), and at least one enzyme specific for a prominent penultimate glycosyl residue (e.g., beta-galactosidase, fucosidase, or mannosidase) on the surface of immune cells. In some embodiments, such enzymes act synergistically with neuraminidase. The regimen does not dysregulate (but instead coordinates) the patient's immune system, which is crucial in fighting infectious disease, and is effective even in the presence of certain levels of cytotoxic chemotherapies, which can have deleterious effects on immune cells. Further, the regimen is applicable for chronic therapy, or repeated therapy, since the agent(s) are not targeted by the immune system in various embodiments. The regimen in various embodiments avoids excess removal of sialic acids or other glycosyl structures from normal cells so that they retain normal function.

In certain embodiments, the glycosidase regimen described herein reduces or eliminates the need for administration of other traditional antiviral or antimicrobial therapies. In various embodiments, the invention finds use in immunocompromised or immunosuppressed patients for increasing immune function. The glycosidase regimen in various embodiments is not immune targeted, and thus the resulting glycosidase signaling can be used for long term therapy.

In one aspect, the invention provides methods for treating patients having a chronic viral infection through a non-acute regimen of a composition comprising a glycosidase formulation that is both tolerated by the immune system ("immune tolerant") and sufficient for stimulating coordinated immune signaling. The glycosidase composition thus provides for immune stimulation, such as through one or more integral immune modulation cascades, while avoiding immune targeting of the glycosidase(s), which would otherwise eliminate its effectiveness over time.

The glycosidase composition and regimen is a cost effective treatment to reverse viral disease state or trajectory, and/or to transition to long term disease management. In some embodiments, the patient is a symptomatic AIDS patient, and the glycosidase composition is provided with, or as an alternative to, ARV therapy, to reverse disease trajectory. While ARVs can be an effective antiviral treatment, ARV's have the adverse effect of suppressing the immune system, an effect harmful particularly for HIV or AIDS patients. Thus, consistent immune modulation through the regimen described herein has the ability to ameliorate these side effects, while in the long term transitioning to the primary disease management. Alternatively or in addition, the glycosidase composition, after amelioration of the condition, allows transition to a cost effective regimen for long term disease management, which in some embodiments eliminates the need for chronic ARV therapy. The regimen is generally effective for managing chronic viral infections such as HIV, HSV, EBV, HAV, HBV, HCV, HPV, adenovirus, and others.

In a second aspect, the invention provides methods of treating and/or preventing an infectious disease. In accordance with this aspect, the patient receives a regimen of the composition described herein, which provides and maintains effective immune stimulation over time, including as a lone or added protection during influenza season, or other ongoing infections disease outbreak or epidemic. In particular embodiments, the invention finds use with immunocompromised patients, including the elderly, children, the sick, hospitalized, and those with an immunodeficiency disorder (including genetic immunodeficiencies, drug-induced immunodeficiency, or due to infections disease such as AIDS). In certain embodiments, the composition and/or regimen acts as an adjuvant to enhance vaccine effectiveness, providing for more effective vaccination and/or longer duration of a vaccine's protective effect and in some embodiments, allows for vaccine dose sparing.

In other aspects, the invention provides a pharmaceutical composition comprising at least two of neuraminidase, galactosidase, N-acetylgalactosaminidase, fucosidase, glucosidase, N-acetylglucosaminidase, and mannosidase, and a pharmaceutically-acceptable excipient. For example, the composition may comprise neuraminidase and β-galactosidase. The glycosidases may be present at, collectively, between about $10^{-3}$ mg to $10^{-8}$ mg. The composition may be formulated for a variety of administration routes, including sublingual delivery.

In still other aspects, the invention provides a convenient glycosidase dose applicator. The applicator delivers a sufficient number of glycosidase doses for a non-acute regimen, such as for example, at least one month of doses for reversing viral disease trajectory or managing an infectious disease, or for preventing or mitigating infectious disease, or enhancing vaccine effectiveness. The applicator maintains stability of the composition over the course of the regimen, protecting the composition from exposure to possible environmental contamination. The glycosidase composition is stable over the length of time needed to administer the doses in accordance with a regimen described herein.

DESCRIPTION OF THE FIGURES

FIG. 3 summarizes the effects of neuraminidase on the production of cytokines in vitro. Cells appropriate for the production and measurement of the respective cytokines were incubated in the presence (experimental) or absence (control) of neuraminidase. For IL-2, IFN-α, and IFN-γ, total cellular RNA was extracted and hybridized with a cytokine-specific radioactive probe and counts per minute were determined. For TNF-α, optical densities were measured in a cell lytic assay. Values for each cytokine are expressed as the percent difference from the corresponding saline control. As indicated by the positive values, all four tested cytokines were stimulated in the presence of neuraminidase relative to controls.

DETAILED DESCRIPTION OF TILE INVENTION

Figure 1:
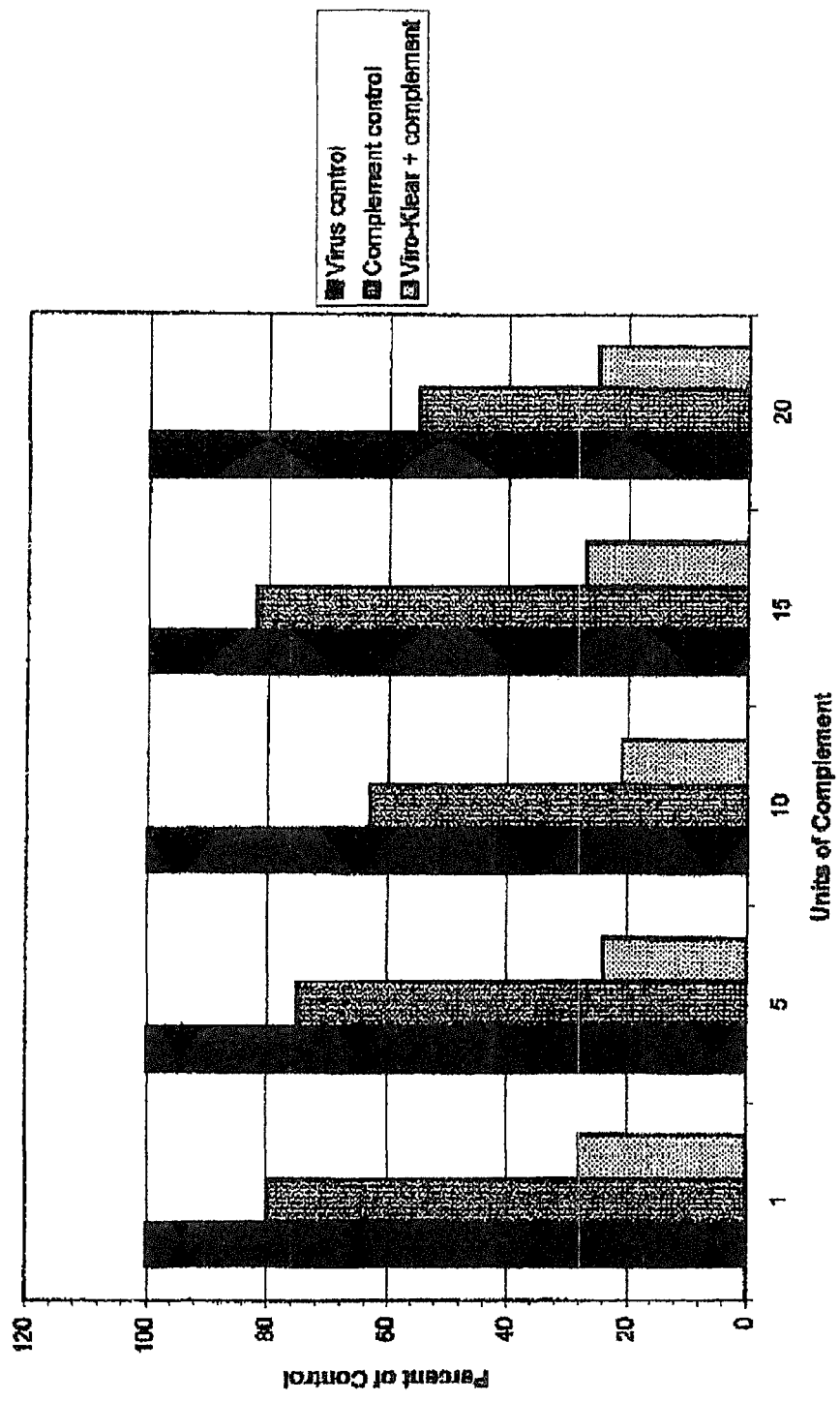
FIG. 1 shows the effect of neuraminidase and complement on the infectivity of Vero cells by HSV-1. The indicated units of complement were incubated with neuraminidase and HSV-1. These mixtures were then added to Vero cell and incubated for 5 days. After cell fixation and staining, plaques were counted, with each plaque corresponding to one initial infectious viral particle. Infectivity is expressed as a percent of the virus control (virus incubated with cells and without complement or neuraminidase).

The present invention provides compositions, methods and treatment regimens for non-acute immune enhancement, which finds application in the treatment of chronic infectious disease, including vaccine (e.g., adjuvant-free vaccine) enhancement.

In one aspect, the invention comprises administering an in vivo regimen of one or more glycosidase enzymes to a patient having an infectious disease. The in vivo regimen stimulates immune signaling through removal of effective amounts of glycosides, notably sialic acids in some embodiments, from the surface of immune cells or other targets, and avoids excess removal of glycosides including sialic acid from normal cells. The regimen allows persistent antigenic targeting of infected cells by the elicited immune cascade. In some embodiments, the regimen comprises enzymes active for removal of glycosides that are prevalent on virally infected cells, and which in various embodiments are terminal or penultimate glycosides. In some embodiments, the regimen comprises neuraminidase and a second glycosidase specific for the removal of a prevalent penultimate glycosyl residue, which can provide a synergistic treatment by avoiding, preventing, or slowing resialylation and/or re-capping of the glycosyl chains. The administration regimen, including as adjunct therapy and including embodiments that involve convenient patient dose monitoring, are as described in detail herein. According to this aspect, the effectiveness of the method does not critically rely on the identity of the infectious agent or the patient's unique biology, unlike many conventional therapies.

The invention in various embodiments provides for administering regimens of a glycosidase composition sufficient for immune stimulation, while also avoiding targeting of the glycosidase by the immune system, which might otherwise reduce or eliminate its effectiveness. In certain aspects, the invention further provides glycosidase dosing applicators for administering the regimens described herein.

In some embodiments, the glycosidase composition comprises neuraminidase, which is an enzyme that hydrolyzes glycosidic linkages of terminal sialic acid residues on various glycoconjugates. Neuraminidases are found in mammalian cells as well as various bacterial, fungal, and viral sources. By virtue of their terminal position on carbohydrate chains of cell membranes, sialic acids are key regulators of communication between cells and of immune recognition phenomena. In accordance with the invention, the neuraminidase is formulated, optionally with other glycosidases as described herein, and provided as a regimen of doses that allows it to function as a signaling cascade immunomodulator, coordinating the host's immune response to effectively combat infectious disease, including HIV and other viral and infectious agents, while not itself being (significantly) targeted by the immune system. In some embodiments, these properties of the composition are improved by proper formulation and/or delivery of the glycosidase.

Figure 2:
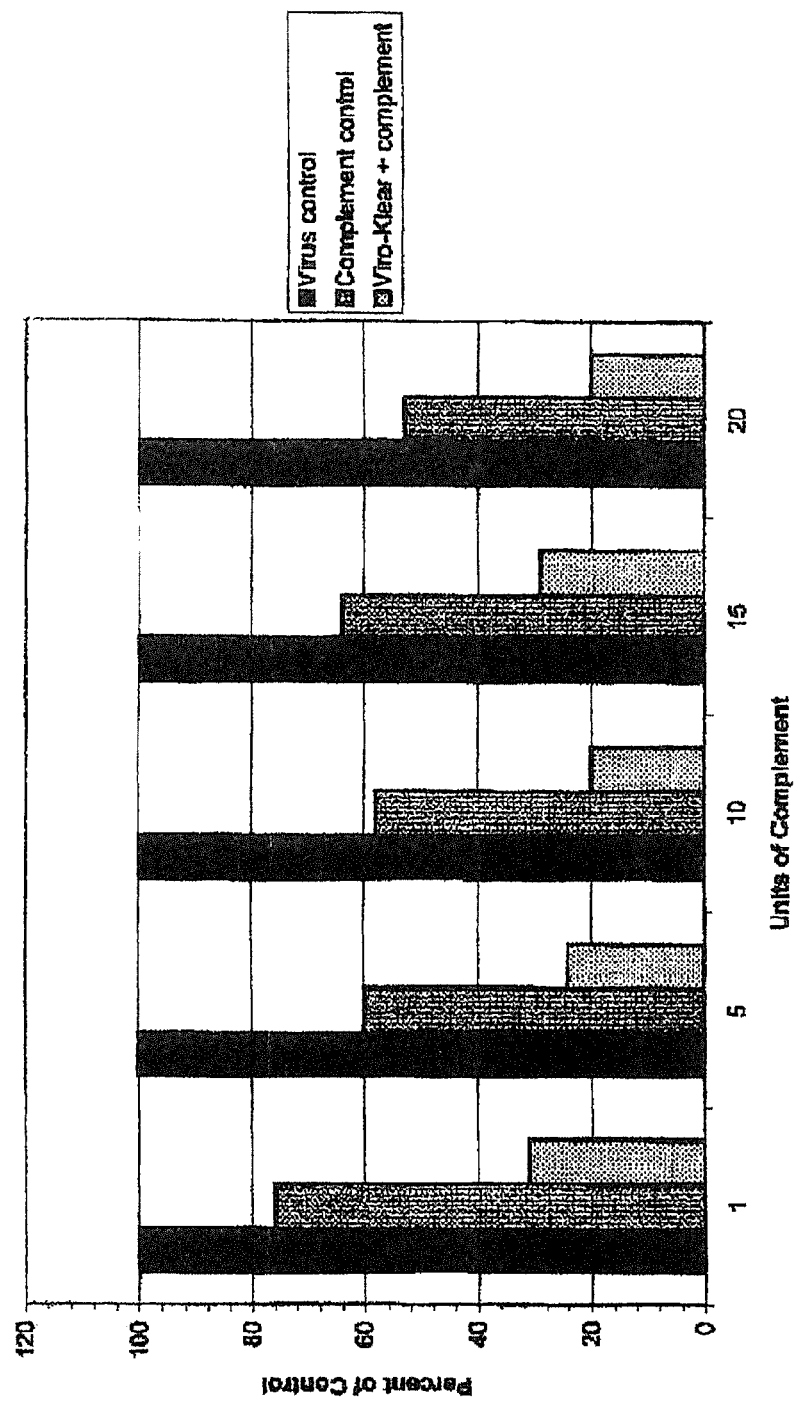
FIG. 2 shows the effect of neuraminidase and complement on the yield of infectious HSV-1 in Vero cells. Vero cells were incubated with HSV-1. These infected cells were then incubated with mixtures containing the indicated units of complement and neuraminidase. Controls consisted of infected cells without complement or neuraminidase (virus control). Following a 24-hour incubation, supernatants (containing released virus) from the cell cultures were tested for their ability to form plaques. Yield is expressed as a percent of the virus control.

In various embodiments, and without wishing to be bound by theory, the glycosidase therapy enhances immune function at least in part by complement activation. For example, when using Herpes simplex (HSV-1) as a model virus, in vitro studies show that incubating proper levels of neuraminidase and complement together significantly reduces both the infectivity of Vero cells by HSV-1 and the release of free virus from pre-infected cells relative to controls (FIGS. 1 and 2).

In various embodiments, and without wishing to be bound by theory, the glycosidase therapy enhances immune function at least in part by cytokine stimulation, including, for example, Interleukin-2 (IL-2), interferon alpha (IFN-α), interferon gamma (IFN-γ), tumor necrosis factor alpha (TNF-α), Interleukin-4 (IL-4), and Interleukin-6 (IL-6). Using in vitro cell systems, the production of at least four cytokines was stimulated in the presence of proper levels of neuraminidase relative to the respective controls. Thus, in some embodiments the functions of these cytokines is enhanced by a maintained or perpetual signal cascade of neuraminidase, leading to control of immune stimulation.

In various embodiments, and without wishing to be bound by theory, the glycosidase therapy enhances immune function at least in part by increasing efficiency of immune cell interactions. The increased efficiency of these immune cell interactions in the presence of proper levels of neuraminidase, as well as other glycosidases, may be due to the removal of negatively charged sialic acid molecules, resulting in greater cell-to-cell contact. In various embodiments, the glycosidase composition and regimen enhances immune function by enhancing cell-mediated cytotoxicity and/or immune cell activation.

In various embodiments, and without wishing to be bound by theory, the glycosidase regimen functions at least in part by increasing exposure of infectious agent, such as virus (e.g., HIV, HSV, EBV, HCV, HPV, adenovirus) and viral infected cells to immune mechanisms. In addition to possible complement activation, removal of terminal sialic acid residues from gp120 of HIV or HIV-infected cells by neuraminidase may have other immune stimulating effects. Removing terminal sialic acid residues and/or other glycans from gp120/gp 160 or HIV either exposes hidden epitopes or alters the conformation of the glycoprotein such that the virus is more susceptible to attack by various components of the host's immune system. The glycosidase formulation and regimen described herein tips the delicate balance between immune defense and viral infectivity in favor of the host.

In various embodiments, without wishing to be bound by theory, the glycosidase regimen, which may comprise one or more of neuraminidase. β-galactosidase, α-mannidase, fucosidase (as well as other glycosidase enzymes, including those described herein) converts vitamin D binding protein (also known as group specific component, or Gel, to an effective macrophage activating factor in vivo, leading to activation of macrophages against the patient's infectious disease. See, for example, U.S. Pat. No. 5,326,749, which is hereby incorporated by reference; Yamamoto et al., *J Immunology* Vol. 151:2794-2802 (1993). Vitamin D-binding protein, also known as DBP, is an evolutionarily conserved glycoprotein, and is genetically polymorphic. DBP has a relative molecular weight of about 52,000, and normally constitutes about 0.5% of the plasma protein. The proper dose and regimen of glycosidase as described herein, can lead to effective, consistent, and chronic in vivo macrophage activation against the particular causative pathogen, including specific targeting of its antigenic state, which is crucial for pathogens that constantly change exposed epitopes. Thus, in vivo administration of the glycosidase composition, including convenient sublingual dosing, leads to effective macrophage activation against pathogens.

In one aspect, the invention provides a method for treating a patient having a chronic viral infection. The method comprises administering a non-acute regimen of an immunotolerant and immune signaling glycosidase composition to the patient so as to treat, ameliorate, and/or manage said infection. In some embodiments, virus is one that integrates with the host genome (e.g., as provirus) or which can become latent, or otherwise escape immune surveillances as to be difficult or impossible to completely eliminate. Exemplary viruses include retroviruses (e.g., HIV), herpes simplex viruses (e.g., HSV-1 or HSV-2), hepatitis viruses (e.g., HAV, HBV, HCV), and adenovirus. In such embodiments, the glycosidase composition and regimen described herein can take the place of antiviral chemotherapy or immunotherapy (e.g., cytokine or chemokine therapy, such as interferon, or monoclonal antibody treatment) for long term disease management, or can be combined with such therapies to improve outcome, that is, either combined simultaneously or in sequence.

In some embodiments, the patient is HIV positive, and in some embodiments is a symptomatic AIDS patient. HIV infection is a worldwide problem, and various governments have made arrangements for their nationals to have access to antiretroviral drugs. In spite of these efforts, sometimes the drugs are not available because of poor communication and poor accessibility which results in missed doses by the patients. Also, quite often, patients are not able to tolerate these drugs. The present invention provides alternatives to antiretroviral drugs in some embodiments, and in other embodiments, provides additional agents to reduce the need for long term use of antiretrovirals or other chemotherapeutic or antiviral therapy.

Thus, in some embodiments, the patient is not undergoing anti-retroviral therapy during the glycosidase treatment, for example, because the patient is unable to tolerate the anti-retroviral therapy, or such ARV therapy is not available to the patient. The HIV may be any sub-type, such as HIV-1 or HIV-2. In some embodiments, the HIV is resistant to anti-retroviral chemotherapy, making the availability of an alternative therapy critical. In some embodiments, the glycosidase is administered or initiated after anti-retroviral therapy to manage chronic AIDS, thereby providing a more effective and cost-sensitive long-term disease management.

The glycosidase regimen may also be administered with anti-retroviral chemotherapy, for example to help reverse disease trajectory. Once disease trajectory is reversed, the glycosidase regimen may be optionally continued for at least one month, at least two months, at least four months, at least six months, or at least one year, or at least two years, or at least five years, or more, to provide a cost-effective management of the disease. The frequency or daily dose may be adjusted for long term treatment as described herein.

In some embodiments, the immune tolerated glycosidase signaling compensates for the loss of CD4 cells, while allowing the host time to recover and replenish its supply of these critical cells. In some embodiments, the glycosidase composition allows a subject on antiretroviral therapy to cease antiretroviral therapy for a period of time (e.g., about one to six months, or about one to four months, or about one to two months), thereby allowing the body to recuperate from the toxic effects of these drugs, while also providing cost advantages. The regimen further allows the immune targeting of the virus and virus particles, as well as infected (e.g., lysogenic) cells preferentially over host cells. In some embodiments, this "cycle" of AVR and glycosidase treatment is repeated one or more times throughout therapy. In still other embodiments, the administration of the glycosidase therapy with anti-retroviral therapy prevents some of the dampening of the immune system often exhibited by retroviral therapy. Administration with other chemotherapeutic regimens, as described in this paragraph, for other viral infections (e.g., HSV-1 or -2, EBV, HAV, HBV, HCV, HPV, adenovirus) can provide for the same or similar advantages.

Drugs designed to combat HIV have focused on the various stages of the viral life cycle. Some have been designed to block the virus' attachment to the CD4 T cell. Others have targeted the various enzymes involved in the assembly stages inside the cell; zidovudine (AZT), for example, is a well-known drug which functions to inhibit the activity of reverse transcriptase, an enzyme HIV uses to copy its RNA genome into DNA. Some of these synthetic drugs have slowed the progression to AIDS, but none have stopped it or eliminated the virus. A major problem has been the high mutation rate of HIV, where drugs initially showing some promise become ineffective as the virus changes its form to one no longer recognized by the drug. The glycosidase regimen also targets HIV mutant derivatives allowing for enhancement of ARV as well as other possible chemotherapies, to reduce the propensity of mutant virus to circumvent the therapeutic.

As used herein, the term anti-retroviral therapy refers to active agents (often cocktails of active agents) administered to HIV and AIDS patients. These include, for example, therapy comprising entry inhibitors (e.g., maraviroc and/or enfuvirtide), CCR5 receptor antagonists, reverse transcriptase inhibitors (e.g., zidovudine, didanosine, zalcitabine, stavudine, foscarnet, and/or lamivudine), protease inhibitors (e.g., ritonavir, darunavir, atazanavir, saquinavir), integrase inhibitors (e.g., raltegravir), maturation inhibitors (e.g., alpha interferon, bevirimat, and/or vivecon). In some embodiments, the retroviral therapy comprises a combination of two nucleoside-analogues and one non-nucleoside-analogue or protease inhibitor. This three drug combination is commonly known as a "triple cocktail." Examples include COMBIVIR (zidovudine+lunivudine), TRIZIVIR (abacavir+zidovudine+lamivudine), KALETRA (lopinavir+ritonavir), EPZICOM (abacavir+lamivudine), TRUVADA (tenofovir+emtricitabine), ATRIPLA (efavirenz+tenofovir+emtricitabine). Other combinations include: tenofovir/emtricitabine/raltegravir, tenofovir/emtricitabine/ritonavir, and darunavir/tenofovir/emtricitabine/ritonavir/atazanavir.

In some embodiments, the anti-retroviral therapy comprises two nucleoside reverse transcriptase inhibitors and one non-nucleotide reverse transcriptase inhibitor. In some embodiments, the ARV therapy comprises Stavudine, Lamivudine, and/or Nevirapine. In some embodiments, the ARV therapy comprises Efavirenz. Such therapies, if administered, are employed sparingly, or to reduce initial disease trajectory, before transitioning to long-term glycosidase treatment. Such long term disease management with glycosidase therapy elicits an immune cascade against free virus, including mutant virus, and infected cells.

The regimen described herein in various embodiments is suitable for treating patients in various stages of AIDS. In some embodiments, the patient's CD4 count at the start of the regimen is less than about 500 coils per $mm^3$. For example, the patient's CD4 count at the start of the regimen may be between about 200 and about 400. The patient's CD4 count at the start of the regimen may be less than about 400, less than about 350, less than about 300, less than about 200, less than about 100, or less than about 50. To some embodiments, where the CD4 count is less than 400, antiretroviral therapy is administered, either alone or with the glycosidase composition, and the glycosidase composition is used for long term care once the CD4 count is normalized (e.g., above about 400 or above about 500 or above about 800). In some embodiments, the patient may continue to have a below normal CD4 count, but the glycosidase composition helps the immune system function with this impairment. In still other embodiments, the patient has a low CD4 count as described, and the glycosidase composition is administered without retroviral therapy, allowing the CD4 count to normalize in the long term.

In some embodiments, the patient's viral load at the start of the regimen is above about 10,000 per ml. For example, the viral load at the start of the regimen may be at least about 25,000 per ml, at least about 40,000 per ml, at least about 50,000 per ml, at least about 75,000 per ml, at least about 100,000 per ml, at least about 500,000 per ml, at least about 1 million per ml, or at least about 5 million per ml. In some embodiments, the patient receives antiretroviral therapy to bring the viral load to less than about 50,000 per ml, or less than 10,000 per ml, or to undetectable, and then transitioning to glycosidase treatment as the long term care. In some embodiments, the combination of antiretroviral therapy and glycosidase allows for faster or more complete reduction in the viral load.

In some embodiments, the benefit of glycosidase therapy is discernable at least in-part through an evaluation of the well being of the patient, including mood and mental state, appetite, energy level secondary infections/complications, hair growth, and other symptoms of improving overall health. Such benefits may or may not be discernable with conventional quantitation of AIDS treatment, such as CD4 level or viral titers.

This glycosidase regimen described herein is applicable to other chronic viral infections. For example, in some embodiments, the patient has a chronic viral infection selected from a herpes simplex virus infection (e.g., HSV-1 or HSV-2), Epstein-Barr Virus infection (e.g., mononucleosis), cytomegalovirus infection, varicella zoster virus infection, hepatitis A, B, or C, adenovirus infection, or human papilloma virus infection. In some embodiments, the patient is diagnosed with chronic fatigue syndrome. The glycosidase composition treats and/or prevents flare-ups of the disease and reduces viral load, and in some embodiments, takes the place of conventional antiviral strategies such as cytokine and/or chemokine therapies (e.g., interferon or interleukin) or small molecule antivirals (e.g., acyclovir, valaciclovir, famciclovir). Alternatively, the glycosidase composition is administered for long term management, once the viral infection is under control by conventional therapy (e.g., interferon or small molecule virus inhibitor or monoclonal antibody therapeutic). In some embodiments, the regimen reduces or eliminates viral lesions such as cold sores, and/or prevents their reoccurrence.

For example, in some embodiments, the patient has an HSV or varicella zoster virus infection, and in some embodiments may have shingles. In accordance with the invention, the patient may not receive antiviral drugs such as acyclovir, valaciclovir and/or famciclovir, or in other embodiments, the glycosidase regimen is administered after the failure of conventional antivirals to ameliorate or eliminate the infection or symptoms thereof, or after conventional antivirals are rules by virtue of the patient's ability to tolerate these drugs.

In still other embodiments, the patient has hepatitis C infection, and receives interferon therapy. In such embodiments, the glycosidase regimen may be provided to replace ineffective INF therapy, for example, once the therapy loses effectiveness or is not tolerated by the patient. In other embodiments, the glycosidase regimen is provided alongside interferon therapy to boost its effectiveness. The glycosidase regimen can facilitate the proper integration of interferon or antibody therapy for an effective immune response.

In a second aspect, the invention provides methods of treating and/or preventing an infectious disease, other than a chronic viral infection described above. In some embodiments, the infectious disease is a persistent or recurrent bacterial infection, such as that associated with pneumonia, bronchitis, sinusitis, vaginitis, enteritis, colitis, sepsis, or urinary tract infection. The regimen is further effective against persistent or recurrent ear, eye, nose and/or throat infection. While the identity of the causative infectious agent is not necessarily crucial, exemplary bacterial agents for which the invention may be effective include species of *Mycobacterium* (including tuberculosis). *Pseudomonas* (e.g., *Pseudomonas aeruginosa*, as may occur in association with cystic fibrosis), *Haemophillus* (e.g., *Haemophillus Influenzae*), *Moraxella, Chlamydia, Neisseria, Streptococcus, Staphylococcus* (including MRSA), *Bordetella, Yersinia*, and others. In some embodiments, the glycosidase regimen is administered after at least one round of antibiotic therapy has failed to ameliorate or eliminate the infection. In some embodiments, the glycosidase regimen is administered alongside antibiotic therapy, to enhance its effects, and reduce the potential for development of resistant bacteria. Exemplary antibiotics in these embodiments include an aminoglycoside, a carbapenum, a cephalosporin, a macrolide, a penicillin (e.g., beta lactam), a quinolone (e.g., a fluoroquinolone such as ciprofloxacin), a sulfonamide, or a tetracycline, or combinations of the above.

In still other embodiments, the glycosidase regimen is effective against fungal or parasitic infections, which may be chronic, persistent, or recurring. Such infections include Candidiasis (e.g., yeast vaginitis), malaria, trypanosomiasis, *Aspergillus* infection, *toxoplasma*, and Giardiasis. The regimen may be administered after unsuccessful chemotherapy or antimicrobial treatment, or may be administered alongside the treatment to increase the rate of successful treatment, including elimination of the infectious agent or symptoms thereof in some embodiments.

In still other embodiments, the glycosidase regimen is administered for prevention of disease, especially where infectious disease is a particular risk, for example, during a Flu, SARS, or other outbreak. In accordance with this aspect, the patient receives a non-acute regimen of the composition described herein, which provides effective glycosidase therapy for a period of time sufficient to span the period of outbreak. For example, the regimen can be administered to a patient at risk of contracting Flu, and the regimen provides for sustained immune stimulation throughout Flu season (e.g., at least two months, at least three months, at least four months, or at least six months). This aspect of the invention is useful for other epidemics or outbreaks, including the protection of healthcare workers who are constantly exposed to highly contagious agents.

In particular embodiments, the invention finds use with immunocompromised patients, including the elderly, the young, the hospitalized, and patients with an immunodeficiency condition (e.g., resulting from AIDS, genetic disorder, or drug treatment), to boost immune function. In certain embodiments, the glycosidase composition and/or regimen acts as a vaccine enhancer, providing for more effective vaccination, and/or longer duration of protective effect and in some embodiments, allows for vaccine dose sparing. In some embodiments, the vaccine is an adjuvant-free vaccine, with the glycosidase composition acting as the adjuvant. For example, the glycosidase composition and regimen may be initiated around the time of receiving a Flu or other vaccine (e.g., initiated within one week or three days or one day of receiving a vaccine), and the glycosidase regimen continued to lengthen the duration of the vaccine's protective effect and/or the level or duration of protective antibody liters.

The glycosidase regimen provides one or more glycosidase enzymes active for removal of one or more terminal and/or penultimate glycosyl groups on mammalian cells (e.g., immune cells and/or virally infected cells). Such terminal and penultimate glycosyl groups include, for example, sialosyl, galactosyl, N-acetylgalactosamino, fucosyl, glucosyl, N-acetylglucosamino, and mannosyl residues. Thus, the glycosidase regimen can include, in various embodiments, one or more of neuraminidase, galactosidase (e.g., β-Galactosidase), N-acetylgalactosaminidase, fucosidase, glucosidase, N-acetylglucosaminidase, and mannosidase.

In some embodiments, the glycosidase regimen comprises neuraminidase treatment. The neuraminidase therapy may employ a neuraminidase or purified fraction having neuraminidase (sialidase) activity, or an active portion or active derivative thereof. In some embodiments, the neuraminidase is microbial (e.g., bacterial, viral, parasitic, or fungal origin). In still other embodiments, the neuraminidase is mammalian or plant. The neuraminidase may be purified from food materials, including microbes that find use in foods, including baker's yeast and *Lactococcus* sp. and *Lactobacillus* sp. In certain embodiments, the neuraminidase is bacterial. The neuraminidase may be purified or isolated from its natural source, or may be recombinant or synthetic (e.g., chemically synthesized). In some embodiments, the neuraminidase is a γ-Group B neuraminidase, also known as exo-α-sialidase, α-Group B, or acetyl Group B, which cleaves terminal sialic acid residues from carbohydrate moieties on the surfaces of host cells and virus. In some embodiments, the neuraminidase catalyzes the hydrolysis of α-2,3, α-2,6 and/or α-2,8 glycosidic linkages of terminal sialic acid residues in oligosaccharides, glycolipids and colominic acid.

For example, in various embodiments, the neuraminidase is an endo or exo sialidase, for example, catalyzing exo hydrolysis of α-(2→3), α-(2→6), and/or α-(2→8) glycosidic linkages of terminal sialic acid residues, or catalyzing endo hydrolysis of (2→8)-α-sialosyl linkages in oligo- or poly(sialic) acid. Exemplary neuraminidase agents include any of the well over 100 known neuraminidase enzymes, or active portion or derivative thereof. In some embodiments, the neuraminidase is an enzyme from one or more of *Closridilum perfringes, Arthrobacter ureafaciens, Vibrio cholerae, Salmonella typhimurium,* or *Streptococcus pneunoniae,* or other whose activities are well characterized. Such neuraminidase enzymes may be purified or isolated from its microbial source, or produced recombinantly or synthetically. See Cassidy J T, *The Sialic Acids—VI, Purification and properties of sialidase from Clostridium perfringes. J Biol. Chem.* 240:9:3501-3506 (1965); Crennell S., et al., *Crystal structure of Vibrio cholerae neuraminidase reveals dual lectin-like domains in addition to the catalytic domain. Structure* 2:535-544 (1994); Uchida et al, *Enzymatic properties of neuraminidases from Arthrobacter ureafaciens. J. Biochem.* 106:1086-1089 (1979), and these references are hereby incorporated by reference. When in purified form, the neuraminidase is at least 10% of the protein component of the composition, at least 25% of the protein component of the composition, 50% of the protein component of the composition, or at least 75% of the total protein component, or at least 90% of the total protein component, or at least 95% of the total protein component, or at least 99% of the total protein component.

Exemplary amino acid sequences for neuraminidase proteins include those defined by GenBank accession numbers: EIA17609.1, EIA17977.1. NP_561469.1, CAA50436.1, (*Clostridium perfringes*), AAX22758.1, BAD66680.2 (*Arthrobacter ureafaciens*), AAW31751.2, AAA27546.1, AEA78761.1 (*Vibrio cholerae*), 2VWO_A (*Streptococcus pneumoniae*), and AAL19864 (*Salmonella typhimurium*), which are each hereby incorporated by reference. The neuraminidase may comprise an amino acid sequence having at least 70%, 80%, 90%, 95%, or more amino acid sequence identity to one or more of the amino acid sequences defined by EIA17609.1. EIA17977.1, NP_561469.1. CAA50436.1, AAX22758.1, BAD66680.2, AAW31751.2, AAA27546.1, AEA78761.1, 2VWO_A., and AAL19864. Additional neuraminidase enzymes are described in U.S. Pat. Nos. 8,012,733, 6,916,916, 5,985,859, 5,830,748, and 4,071,408, which descriptions are hereby incorporated by reference in their entireties.

Suitable neuraminidases can be obtained from commercial sources. Exemplary neuraminidase enzymes include Sigma Aldrich product numbness N2876, N3001, N5631, N2133 (*Clostridium perfringes*), N7885, N6514 (*Vibrio cholerae*), N3786, and N8271 (*Arthrobacter ureafaciens*).

Preparation of derivatives or mutants of these or other neuraminidase enzymes may be guided by any of the known structures or studies, including those described by: Kim S et al., *Features and applications of bacterial sialidase, Appl Microbiol Biotechnol.* 2011, 91(1):1-15; Crennell S J, et al., *Crystal structure of a bacterial sialidase (from Salmonella typhimurium LT2) shows the same fold as an influenza virus neuraminidase, Proc Natl Acad Sci USA* 1993 90(21):9852-6; Chavas L M, *Crystal structure of the human cytosolic sialidase Neu2: Evidence for the dynamic nature of substrate recognition*. J Biol Chem. 2005 280(1):469-75; Xu G et al, *Crystal structure of the NanB sialidase from Streptococcus pneumoniae, J Mol Biol.* 2008 384(2):436-49; Newstead S L, et al., *The structure of Clostridium perfringens NanI sialidase and its catalytic intermediates, J Biol Chem.* 2008 283(14):9080-8; (Chan J, et al., *Bacterial and viral sialidase: contribution of the conserved active site glutarnate to catalysis. Biochemistry* 2012 51(1):433-41; Chien C H, et al., *Site-directed mutations of the catalytic and conserved amino acids of the neuraminidase gene, nanH, of Clostridium perfringes ATCC* 10543, *Enzyme Microb. Technol.* 19(4):267-276 (1996); Christensen and Egebjerg, *Cloning, expression and characterization of a sialidase acne from Arthrobacter ureafaciens, Biotechnol. Appl. Biochem.* 41:225-231 (2005). These references are each hereby incorporated by reference in their entireties.

Neuraminidase activity can generally be described in terms of units (U), by determining the amount of sialic acid released from a suitable substrate, under defined conditions (e.g., pH 5.0 and 37° C.). An exemplary substrate is NAN-lactose or bovine submaxillary mucin. See Warren L, *J Biol. Chem.* 234 1971 (1959).

In those and other independent embodiments, the glycosidase regimen comprises galactosidase administration, which in some embodiments is β-galactosidase. Galactosidase may be co-formulated with neuraminidase or other enzyme in embodiments involving two or more glycosidase enzymes. Alpha- or Beta-galactosyl residues (including 1→3 linked and 1→4 linked) act as terminal glycosides on mammalian cells, including immune cells, and/or may be penultimate glycosyl residues, and may be linked to terminal sialic acids in some instances. Hakomori, *Aberant Glycosylation in Cancer Cell Membranes as Focused on Glycolipids: Overview and Perspectives, Cancer Research* 45, 2405-2414 (1985); Dwek and Brooks, *Harnessing Changes in Cellular Glycosylation in New Cancer Treatment Strategies, Current Cancer Drug Targets* 4:425442 (2004). Thus, galactosidase (e.g., β-galactosidase) may be used independently according to the methods described herein, or may be used in conjunction with neuraminidase or other glycosidase, which in some embodiments, prevents or slows resialylation or recapping of glycosyl structures, thus rendering the regimen more effective, and supporting less frequent administrations and/or lower dosing.

Exemplary galactosidases are well known and commercially available. For example, β-Galactosidase may be obtained from *Escherichia coli, Aspergillus, oryzae, Kluyveromyces lactis*, and *Streptococcus pneumoniae*, as well as other microbial (e.g., bacterial or fungal) and biological sources, including mammalian sources. For example, a suitable β-galactosidase may be obtained from Sigma-Aldrich catalogue number 05635.

In these and other independent embodiments, the glycosidase regimen comprises N-acetylgalactosaminidase administration, N-acetylgalactosaminidase may be co-formulated with neuraminidase or other enzyme in embodiments involving two or more glycosidase enzymes. Hakomori, *Aberant Glycosylation in Cancer Cell Membranes as Focused on Glycolipids: Overview and Perspectives, Cancer Research* 45, 2405-2414 (1985); Dwek and Brooks, *Harnessing Changes in Cellular Glycosylation in New Cancer Treatment Strategies, Current Cancer Drug Targets* 4:425-442 (2004), N-acetylgalactosaminidase may be used independently according to the methods described herein, or may be used in conjunction with neuraminidase or other glycosidase, which in some embodiments, prevents or slows resialylation or recapping of glycosyl chains.

Exemplary N-acetylgalactosaminidases are well known and commercially available. For example, β-N-acetylgalactosaminidase may be obtained from *Bacillus* sp., as well as other microbial (e.g., bacterial or fungal) and biological sources, including mammalian sources. For example, a suitable β-N-acetylgalactosaminidase may be obtained from Sigma-Aldrich catalogue number A2464.

In these and other independent embodiments, the glycosidase regimen comprises fucosidase administration, which is some embodiments is α-fucosidase. Fucosidase may be co-formulated with neuraminidase or other enzyme in embodiments involving two or more glycosidase enzymes (e.g., co-formulated with galactosidase or N-acetylgalactosaminidase). Fucosyl residues (including α1→2 linked, α1→3 linked, and α1→4 linked) act as terminal glycosides on mammalian cells, including immune cells, and/or may be penultimate glycosyl residues, and may be linked to terminal sialic acids in some instances. Hakomori, *Aberant Glycosylation in Cancer Cell Membranes as Focused on Glycolipids: Overview and Perspectives, Cancer Research* 45, 2405-2414 (1985): Dwek and Brooks, *Harnessing Changes in Cellular Glycosylation in New Cancer Treatment Strategies, Current Cancer Drug Targets* 4:425-442 (2004). Thus, fucosidase (e.g., α-fucosidase) may be used independently according to the methods described herein, or may be used in conjunction with neuraminidase, which in some embodiments, prevents or slows resialylation re-capping of glycosyl chains, thus rendering the regimen more effective, and supporting less frequent administrations and/or lower dosing.

Exemplary fucosidase enzymes are well known and commercially available. For example, α-fucosidase may be obtained from *Xanthomonas* sp. (e.g., manicottis), as well as other microbial (e.g., bacterial or fungal) and biological sources. Including mammalian sources. For example, a suitable α-fucosidase may be obtained from Sigma-Aldrich catalogue numbers F3023 and F1924.

In these and other independent embodiments, the glycosidase regimen comprises glucosidase administration, which in some embodiments is α-glucosidase. Glucosidase may be co-formulated with neuraminidase or other enzyme in embodiments involving two or more glycosidase enzymes (e.g., co-formulated with neuraminidase, mannosidase, or N-acetylglucosaminidase). Glycosyl residues (including α1→2 linked, α1→3 linked, and α1→4 linked) act as terminal glycosides on mammalian cells, including immune cells, and/or in some instances may be internal glycosyl residues. Hakomori, *Aberant Glycosylation in Cancer Cell Membranes as Focused on Glycolipids: Overview and Perspectives, Cancer Research* 45, 2405-2414 (1985); Dwek and Brooks, *Harnessing Changes in Cellular Glycosylation in New Cancer Treatment Strategies. Current Cancer Drug Targets* 4:425-442 (2004). Thus, glucosidase (e.g., α-glucosidase) may be used independently according to the methods described herein, or may be used in conjunction with neuraminidase, mannosidase, or other glycosidase, which in some embodiments, prevents or slows resialylation re-capping of glycosyl chains, thus rendering the regimen more effective, and supporting loss frequent administrations and/or lower dosing.

Exemplary glucosidase enzymes are well known and commercially available. For example, α-glucosidase may be obtained from *Sacchromyces cerevisiae, Aspergillus niger*, or *Bacillus stearothermophilus*, as well as other microbial (e.g., bacterial or fungal) and biological sources (including food sources such as rice), and including mammalian sources. For example, a suitable α-glucosidase may be obtained from Sigma-Aldrich catalogue numbers G5003, G0660, 70797, 49291, G9259, and G3651.

In these and other independent embodiments, the glycosidase regimen comprises N-acetylglucosaminidase administration, which is some embodiments is β-N-acetylglucosaminidase, N-acetylglucosaminidase may be co-formulated with neuraminidase or other enzyme in embodiments involving two or more glycosidase enzymes (e.g., co-formulated with neuraminidase, mannosidase, and/ or glucosidase), N-acetylglucosamine residues (including β1→4 linked, β1→6 linked, and others) act as terminal glycosides on mammalian cells, including immune cells, and/or in some instances may be penultimate or internal glycosyl residues. Hakomori, *Aberant Glycosylation in Cancer Cell Membranes as Focused on Glycolipids: Overview and Perspectives, Cancer Research* 45, 2405-2414 (1985); Dwek and Brooks, *Harnessing Changes in Cellular Glycosylation in New Cancer Treatment Strategies. Current Cancer Drug Targets* 4:425-442 (2004). Thus, N-acetylglucosaminidase (e.g., β-N-acetylglucosaminidase) may be used independently according to the methods described herein, or may be used in conjunction with neuramiudase, mannosidase, of glucosidase, which in some embodiments, prevents or slows resialylation re-capping of glycosyl chains, thus rendering the regimen more effective, and supporting less frequent administrations and/or lower dosing.

Exemplary N-acetylglucosaminidase enzymes are well known and commercially available. For example, β-N-acetylglucosaminidase may be obtained from *Streptococcus pneumoniae* and *Canavalia ensiformis*, as well as other microbial (e.g., bacterial or fungal) and biological sources (including food sources), and including mammalian sources. For example, a suitable β-N-acetylglucosaminidase may be obtained from Sigma-Aldrich catalogue numbers A2264 and A6803.

In these and other independent embodiments, the glycosidase regimen comprises mannosidase administration, which in some embodiments is α-mannosidase. Mannosidase may be co-formulated with neuraminidase or other enzyme in embodiments involving two or more glycosidase enzymes (e.g., co-formulated with neuraminidase, glucosidase, and/ or N-acetylglucosaminidase). Mannosyl residues (including α1→2 linked, α1→3 linked, α1→6 linked, β1→4 linked, and others) act as terminal glycosides on mammalian cells, including immune cells, and/or in some instances may be penultimate or internal glycosyl residues. Hakomori, *Aberant Glycosylation in Cancer Cell Membranes as Focused on Glycolipids: Overview and Perspectives, Cancer Research* 45, 2405-2414 (1985); Dwek and Brooks, *Harnessing Changes in Cellular Glycosylation in New Cancer Treatment Strategies, Current Cancer Drug Targets* 4:425-442 (2004). Thus, mannosidase (e.g., α-mannosidase) may be used independently according to the methods described herein, or may be used in conjunction with neuraminidase, glucosidase, and/or N-acetylglucosaminidase, which in some embodiments, prevents or slows resialylation re-capping of glycosyl chains, thus rendering the regimen more effective, and supporting less frequent administrations and/ or lower doing.

Exemplary mannosidase enzymes are well known and commercially available. For example, mannosidase may be obtained from *Canavalia enformis* (α) or *Helix pomatia* (β), as well as other microbial (e.g., bacterial or fungal) and biological sources (including food sources), and including mammalian sources. For example, a suitable mannosidase may be obtained from Sigma-Aldrich catalogue numbers M7257 or M9400.

Administration of effective amounts of formulated glycosidase to a human or animal aids in the prevention or elimination of infectious disease symptoms through modulation of the immune function and/or direct action on the infected cells or other tissues or cells involved in the pathology. The glycosidase enzymes are administered at a dose and frequency so as to exhibit a reduction in symptoms or pathology, without impacting normal cellular functions. The dose and/or frequency of administration in some embodiments is a dose and/or frequency that does not cause prolonged joint discomfort or malaise (e.g., a general feeling of discomfort). Where joint or general discomfort is experienced by the patient, the patient may adjust the dose or frequency of administration until the discomfort subsides or normalizes. For example, where the patient experiences discomfort, the patient may skip one, two, or three days of dosing, and/or subtract one or two daily doses from the regimen, and/or increase the timing between doses, until the discomfort subsides or normalizes. Thus, the patient finds the highest dose and/or frequency of administration that Induces no prolonged joint discomfort, or minimal discomfort. In some embodiments where the amount of dose is controllable, for example using a metered dose applicator, the dose may be reduced but the schedule maintained. Thus, each patient can tailor the dose as needed given the state of the patient's unique biology, disease or immune system condition, by finding the highest dose/frequency that does not induce prolonged joint discomfort or malaise. In practice, the glycosidase formulation may be administered at less than approximately $10^{-2}$ or less than about $10^{-3}$ mg per dosage unit to a human or animal. In certain embodiments, the glycosidase(s) are administered at between approximately $10^{-3}$ mg to $10^{-6}$ mg. In still other embodiments, the dose of glycosidase is between approximately $10^{-3}$ mg and $10^{-7}$ mg, $10^{-3}$ mg and $10^{-6}$ mg, $10^{-3}$ mg and $10^{-5}$ mg, or is approximately $10^{-4}$ mg. In some embodiments, the total daily dose does not exceed about $10^{-3}$ mg per subject, or in some embodiments, does not exceed from about $5\times10^{-3}$ to $10^{-4}$ mg. Generally, patients exhibiting immune suppression (such as those receiving ARVs) may require higher doses within the range of $10^{-2}$ or $10^{-3}$ mg.

While certain glycosidases, including neuraminidases, can have a tendency to form homodimers (e.g., trimers, tetramers), in various embodiments the glycosidase(s) are formulated (e.g., diluted) to be present as a monomer and/or dimer, with substantially no higher aggregates as determinable by size exclusion chromatography (SEC).

The glycosidase(s) may be formulated as an aqueous formulation, including for sublingual, nasal, or buccal delivery. In some embodiments, the aqueous formulation comprises saline. In some embodiments, the formulation has the ionic strength of from about 0.5 to about 2% saline, such as the ionic strength of about 0.9%, saline. In some embodiments, the glycosidase(s) are formulated in normal saline (e.g., about 0.9% saline). Other conventional carriers for sublingual, nasal, or buccal delivery may also be employed. The glycosidase(s) may be further formulated with a preservative, which may be an aromatic or phenolic preservative. For example, the preservative in some embodiments is phenol. For example, in some embodiments neuraminidase, optionally with other glycosidases, is formulated in 0.05 to 0.5% phenol, or comparable amounts of similar acting preservative, for example. In some embodiments, the activity of the neuraminidase and potentially other glycosidases is increased by the presence of phenol, such as at least 02%, 0.3%, or 0.4% phenol. In some embodiments the neuraminidase (e.g., Sigma Aldrich catalogue numbers N2876, N3001, N5631, N2133, N7885, N6514, N3786, N8271) is incubated in a solution containing from about 0.2% to about 1% phenol (e.g., from 0.2 to 0.6% phenol, or about 0.4% phenol), and then diluted to or brought to the final formulation, which may contain from 0.05% to about 0.2% phenol. In some embodiments, such "activation" of the neuraminidase allows the active agent to be administered in lower doses to avoid immune targeting, while maintaining the proper level of activity.

For illustration, neuraminidase and optionally with other glycosidase enzyme(s), can be mixed with 0.9% saline, and filter sterilized, and allowed to stand at room temperature for from 10 minutes to five hours (e.g., about 30 minutes to about three hours). After the incubation at room temperature, phenol saline is added to give a final phenol concentration of about 0.1% in 0.9% saline solution. The solution is stored at 4° C.

Alternatively, neuraminidase and optionally other glycosidase enzyme(s) is mixed with about 0.4% phenol saline. This solution is filter sterilized, and allowed to stand at room temperature for from 5 minutes to about 5 hours (e.g., about 30 minutes, about one hour, or about three hours). After the incubation at room temperature, the final concentration is brought to about 0.1% phenol, 0.9% saline. The solution is stored at 4° C.

The glycosidase formulation may be administered by a variety of routes, including sublingual, nasal, port, subdermal, gavage, intraocular, intravenous, intramuscular, subcutaneous, transdermal, and buccal. In various embodiments, the glycosidases are administered sublingually. In some embodiments in which the glycosidase is administered sublingually, the neuraminidase is held under the tongue for from about one to about five minutes, and preferably for about 3, about 4, or about 5 minutes. The patient should refrain from speaking during this time. The patient should lot eat or drink within 15 minutes of administration.

In accordance with aspects of the invention, regimens of glycosidase enzyme(s) are administered on average from 2 to 6 times per day for at least two weeks or at least one month, especially for the immune compromised or advanced cases. The daily administrations should be substantially evenly spaced, but in various embodiments are spaced by about 15 minutes to 5 hours. For example, doses may be spaced by about 15 minutes, about 30 minutes, about 1 hour, about 2 hours, or about 3 hours. For example, the glycosidase formulation may be administered on average from 2 to 8 times per day for at least about two months, at least about four months, or at least about five months, or at least about six months. In some embodiments, the glycosidase formulation is administered about 2, about 3, or about 4 times per day over at least one month, two months, three months, four months, five months, or six months. Generally, the glycosidase formulation is administered at a dose and frequency so as to be effective in reducing the infectious disease pathology or stimulating the immune system, without exhibiting substantial prolonged joint discomfort or malaise. Where the patient does experience joint or general discomfort, the patient adjusts the dose and/or frequency (e.g., skips one, two or three days of neuraminidase dosing, or reduces the daily dose by one or two administrations), until the discomfort subsides or normalizes. Thus, the administration regimen is suspended during times of joint discomfort in some embodiments.

For example, the first day of treatment may begin with about eight doses, the first three to five taken in the first one or two hours, with the remainder approximately evenly spaced throughout the day. The patient may then be treated with about four doses per day, with periodic monitoring of the malignancy. Even where the malignancy is undetectable, the patient may remain on a regimen of 2 to 7 doses per day, as adjusted from time to time based on the appearance of joint discomfort or malaise.

Therapy may be initiated as described above. However, in some embodiments, the glycosidase regimen is an alternative to these conventional therapies. In some embodiments, the patient is subsequently treated chronically with about one dose per day, for at least about six months, or at least about one year, or at least about two years, or at least about five years, or more, or is selected or prescribed for such chronic treatment.

This subsequent chronic treatment in some embodiments is with the absence of chemotherapeutic or other therapy to reduce the likelihood of recurrence or disease progression. Chronic glycosidase treatment, for example, to prevent disease recurrence or relapse, may be administered 1 or 2 times per day.

In some embodiments, the patient is instructed to monitor joint stiffness or malaise. Such conditions suggest that glycosidase treatment should be adjusted. The adjustment may include skipping one or two days or up to one week of dosing, or alternatively lowering the dose by one or two administrations per day, until the symptoms clear. Other molecular assays could be used to the same effect, although joint stiffness or discomfort provides an case of patient compliance. Thus, over the course of the regimen, the glycosidase dose can be easily adjusted per patient, and thus maintained chronically for optimal care.

In still other aspects of the invention there is provided a pharmaceutical composition comprising a delivery vehicle for administering a single glycosidase dose upon demand, and where the vehicle contains a full glycosidase regimen of at least 50 doss, or at least 100 doses, at Least 150 doses, or at least 200 doses. Each dose of glycosidase administered is an amount of up to about $10^{-2}$ mg glycosidase and pharmaceutically inert ingredients as already described. The pharmaceutical composition may comprise at least two of neuraminidase, galactosidase, N-acetylgalactosaminidase, fucosidase, glucosidase, N-acetylglucosaminidase, and mannosidase, and a pharmaceutically-acceptable excipient. For example, the composition may comprise neuraminidase and β-galactosidase. The glycosidases may be present at, collectively, between about $10^{-3}$ mg to $10^{-8}$ mg, or according to the doses disclosed above. The composition may be formulated for a variety of administration routes as disclosed herein, including sublingual delivery.

In various embodiments, the treatment regimen involves the partitional administration of an amount not to exceed approximately $10^{-3}$ mg of glycosidase, although, in certain cases, the total amount of glycosidase administered in any one day may exceed this limit.

The glycosidase formulation can be administered in a variety of routes and forms. For example, the glycosidase can be administered as a solid where the enzymes are embedded or admixed in a biodegradable or bioerodible matrix. The matrix can be a time release matrix. These matrices are well known to those of ordinary skill in the art. The glycosidase can be administered by injection or by sublingual route. In one embodiment, the vehicle is an aqueous solution that is contained within an inert container. In another variation, the composition is in the form of a suppository. The liquid form of the composition can be injected subcutaneously, intramuscularly or intravenously. In addition, the composition can be administered through the mucosal membranes such as nasal membranes.

In certain embodiments, the glycosidase composition is administered via a drug applicator, the applicator comprising at least 100 doses of the composition, or at least 150 doses, or at least 200 doses. In various embodiments, the applicator is for sublingual, nasal, transdermal, time release sub-dermal, intraocular, gavage, port, subcutaneous, oral, or buccal delivery. For example, the applicator is for sublingual delivery.

In some embodiments, the applicator delivers a metered dose, that can be adjusted by the patient as needed.

The applicator preferably dispenses doses in a manner that maintains aseptic conditions of the remaining doses. By way of non-limiting examples, the applicator can be any of those that are described in U.S. Pat. Nos. 4,830,284; 4,565,302; 5,011,046; 5,147,087; 5,893,484; 6,877,672; 6,886,556, and 7,201,296, which are each hereby incorporated by reference in their entireties. For instance, the applicator can be an atomizing or dosing pump, which can ensure that the medium present in the area between the pump cylinder and the discharge opening does not dry or is not otherwise altered by ambient influences. See U.S. Pat. No. 4,830,284 which is hereby incorporated by reference. In some embodiments, the applicator employs a 0.2 μm filter to maintain aseptic contents. Additionally, the applicator can dispense doses in a single-stroke discharge. Such applicators are described in U.S. Pat. No. 5,893,484, which is hereby incorporated by reference. The applicator may be configured for nasal delivery, dermal delivery, throat delivery, or sublingual delivery. In some embodiments, the applicator allows for an actuatable dosing mechanism, which permits monitoring of precise doses and therefore largely eliminates incorrect dosing with respect to the number of doses and/or the duration dosing. See U.S. Pat. No. 4,565,302, which is hereby incorporated by reference. In some embodiments, the applicator delivers a dose in from 50 to 100 μl, such as the applicators described in, for example, U.S. Pat. No. 6,886,556, which is hereby incorporated by reference.

EXAMPLES

Example 1: Effect on HSV-1 Infectivity

Using HSV-1 as model virus, in vitro studies were initiated to determine the effect of neuraminidase and complement on viral infectivity and release from Vero cells. For infectivity studies, combinations of complement, virus and neuraminidase were incubated together, then added to Vero cells and incubated further. Following cell fixation and staining, the virus-forming plaques in the cells were counted. Results showed that incubating the virus with neuraminidase and complement together significantly (70-80%) reduced the virus' infectivity of Veto cells relative to controls (FIG. 1).

For Viral release studies. Vero cells were first infected with HSV-1. These cells were then incubated with various concentrations of complement and neuraminidase. Supernatants from the cell cultures were tested for plaque-forming ability, indicative of virus released from the cells. Results showed that, in the presence of both neuraminidase and complement, the release of free virus was greatly decreased (70-80%) relative to controls (FIG. 2). These results indicate that a combination of neuraminidase and complement effectively reduced both the infectivity of Vero cells by HSV-1 and the release of free virus from pre-infected cell.

Example 2: Effect on Cytokine Release

The effect of neuraminidase on the production of certain cytokines in vitro was investigated. Cytokines are chemical messengers secreted by activated lymphocytes in response to infection. Any given cytokine, either alone or in combination with other cytokines, can have multiple effects on immune function. Interleukin-2 (TL-2), interferon alpha (IFN-α), interferon gamma (IFN-γ and tumor necrosis factor alpha (TNF-α) are important cytokines involved in host defense against viruses. IL-2, TNF-α and IFN-γ are produced by the T-helper (TH1) subset of T cells and are therefore associated with the inflammatory process. IL-2 and IFN-γ together activate macrophages, which are important immune cells that engulf and digest pathogens (phagocytosis), and also serve as antigen-presenting cells to T lymphocytes. IL-2 and IFN-γ also enhance the cytotoxicity of natural killer (NK) cells in clearing virally-infected cells. IFN-γ also enhances the expression of major histocompatibility complex (MHC) class I and II molecules on antigen-presenting cells, thereby inducing CD4+ and CD8+ cytolytic cells involved in viral clearance. IFN-γ also combines with TNF-α to stimulate NK cells. IFN-α inhibits viral replication by blocking the transcription of early viral proteins.

These cytokines were studied in vitro using cell systems, incubation conditions and other procedures appropriate for the production and measurement of the respective molecules. Experimental samples containing neuraminidase were compared to saline controls. FIG. 3 summarizes the results obtained when cells treated with neuraminidase were tested for the production of IL-2, IFN-α, IFN-γ, and TNF-α. The production of all four cytokines was stimulated using the therapeutic dose of neuraminidase relative to the respective controls. It is reasonable to expect that the functions of these cytokines discussed above could be enhanced by neuraminidase in an in vivo system, and would have antiviral effects in patients.

The invention claimed is:

1. A method for treating a patient having a chronic viral infection, comprising administering a regimen of a glycosidase composition comprising neuraminidase to said patient so as to treat, ameliorate, and/or manage said infection, wherein the neuraminidase is a *Clostridium perfringens* NanI neuraminidase, and wherein the composition delivers $10^{-3}$ to $10^{-8}$ mg of glycosidase per dose.

2. The method of claim 1, wherein the neuraminidase is recombinant.

3. The method of claim 1, wherein the composition further comprises one or more of β-galactosidase, N-acetylgalactosidase, fucosidase, glucosidase, N-acetylglucosaminidase, and mannosidase.

4. The method of claim 3, wherein the composition further comprises β-galactosidase.

5. The method of claim 1, wherein the glycosidase composition is administered sublingually.

6. The method of claim 1, wherein the patient is HIV positive.

7. The method of claim 6, wherein the patient has AIDS.

8. The method of claim 6, wherein the patient is not undergoing antiviral chemotherapy, and/or the HIV is resistant to antiviral therapy.

9. The method of claim 7, wherein the regimen is initiated after antiviral therapy to manage chronic AIDS.

10. The method of claim 7, wherein the composition is administered with antiviral therapy to reverse disease trajectory.

11. The method of claim 7, wherein the patient's CD4 count at the start of said regimen is less than 500.

12. The method of claim 11, wherein the patient's CD4 count at the start of said regimen is less than 400.

13. The method of claim 6, wherein the viral load at the start of said regimen is above 10,000 per ml.

14. The method of claim 1, wherein the patient has a chronic viral infection selected from a herpes simplex virus infection, varicella zoster virus infection, hepatitis A, B, or C, adenovirus infection, and human papilloma virus infection.

15. The method of claim 14, wherein the patient has shingles.

16. The method of claim 1, wherein the glycosidase is administered on average from 2 to 6 times per day for at least one month.

17. The method of claim 16, wherein the glycosidase is administered on average from 2 to 6 times per day for at least six months.

18. The method of claim 16, wherein the patient is subsequently treated chronically with about one dose per day for at least six months.

19. The method of claim 1, wherein the composition delivers from $10^{-3}$ to $10^{-6}$ mg of glycosidase per dose.

20. The method of claim 1, wherein the frequency of dosing is selected to reduce disease symptoms while not causing prolonged joint discomfort.

* * * * *